(12) United States Patent
Dolle et al.

(10) Patent No.: US 6,225,425 B1
(45) Date of Patent: May 1, 2001

(54) SYNDIO-ISOBLOCK POLYMER AND PROCESS FOR ITS PREPARATION

(75) Inventors: Volker Dolle, Kelkheim/Taunus; Jürgen Rohrmann, Liederbach; Andreas Winter, Kelkheim/Taunus; Martin Antberg, Hofheim am Taunus; Robert Klein, Frankfurt am Main, all of (DE)

(73) Assignee: Targor GmbH (DE)

( * ) Notice: Subject to any disclaimer, the term of this patent is extended or adjusted under 35 U.S.C. 154(b) by 0 days.

(21) Appl. No.: 08/147,006

(22) Filed: Nov. 1, 1993

Related U.S. Application Data

(60) Continuation of application No. 07/927,869, filed on Aug. 10, 1992, now abandoned, which is a division of application No. 07/525,096, filed on May 17, 1990, now abandoned.

(30) Foreign Application Priority Data

May 20, 1989 (DE) ................................. 39 16 553

(51) Int. Cl.$^7$ ............................................. C08F 4/64
(52) U.S. Cl. .................. 526/127; 502/117; 502/152; 526/160; 526/351; 526/943; 556/7; 556/9; 556/11; 556/12; 556/13; 556/43; 556/53
(58) Field of Search ................... 526/127, 160, 526/351, 943; 502/117, 152; 556/7, 9, 11, 12, 13, 43, 53

(56) References Cited

U.S. PATENT DOCUMENTS

| | | | |
|---|---|---|---|
| 3,258,455 | * 6/1966 | Natta et al. | 526/351 |
| 4,522,982 | 6/1985 | Ewen . | |
| 4,542,199 | 9/1985 | Kaminsky et al. . | |
| 4,769,510 | 9/1988 | Kaminsky et al. . | |
| 4,841,004 | * 6/1989 | Kaminsky et al. | 526/160 |
| 4,849,487 | * 7/1989 | Kaminsky et al. | 526/351 |
| 4,892,851 | * 1/1990 | Ewen et al. | 526/351 |
| 5,036,034 | * 7/1991 | Ewen | 526/351 |
| 5,132,381 | * 7/1992 | Winter et al. | 526/351 |

FOREIGN PATENT DOCUMENTS

| | | |
|---|---|---|
| 0069951 | 1/1983 | (EP) . |
| 0185918 | 7/1986 | (EP) . |
| 0269986 | 6/1988 | (EP) . |
| 0269987 | 6/1988 | (EP) . |
| 0344887 | 12/1989 | (EP) . |
| 0351392 | 1/1990 | (EP) . |

OTHER PUBLICATIONS

Farina et al (I), Macromolecules 1982, 15, 1451–1452.*
Farina et al (II), Macromolecules 1985, 18, 923–928.*
Difilvestro et al, Macromolecules 1985, 18, 928–932.*
Ewen, J.A. et al, *J.Am.Chem.Soc* 110:6255–6256 (1988).

* cited by examiner

Primary Examiner—David W. Wu
(74) Attorney, Agent, or Firm—Connolly Bove Lodge & Hutz LLP

(57) ABSTRACT

Syndio-isoblock polymers of 1-olefins having molecular chains which contain syndiotactic and isotactic sequences are obtained if the polymerization of the 1-olefins is carried out using a catalyst which is composed of a bridge chiral metallocene of the formula I

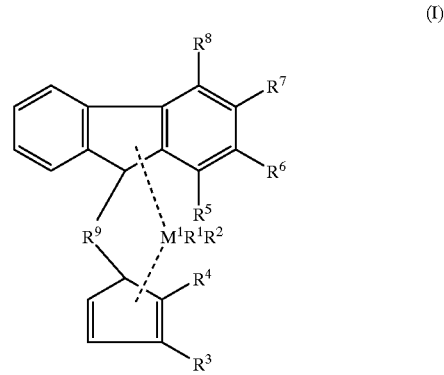

an an aluminoxane. The polymers have some rubber-like properties.

26 Claims, 1 Drawing Sheet

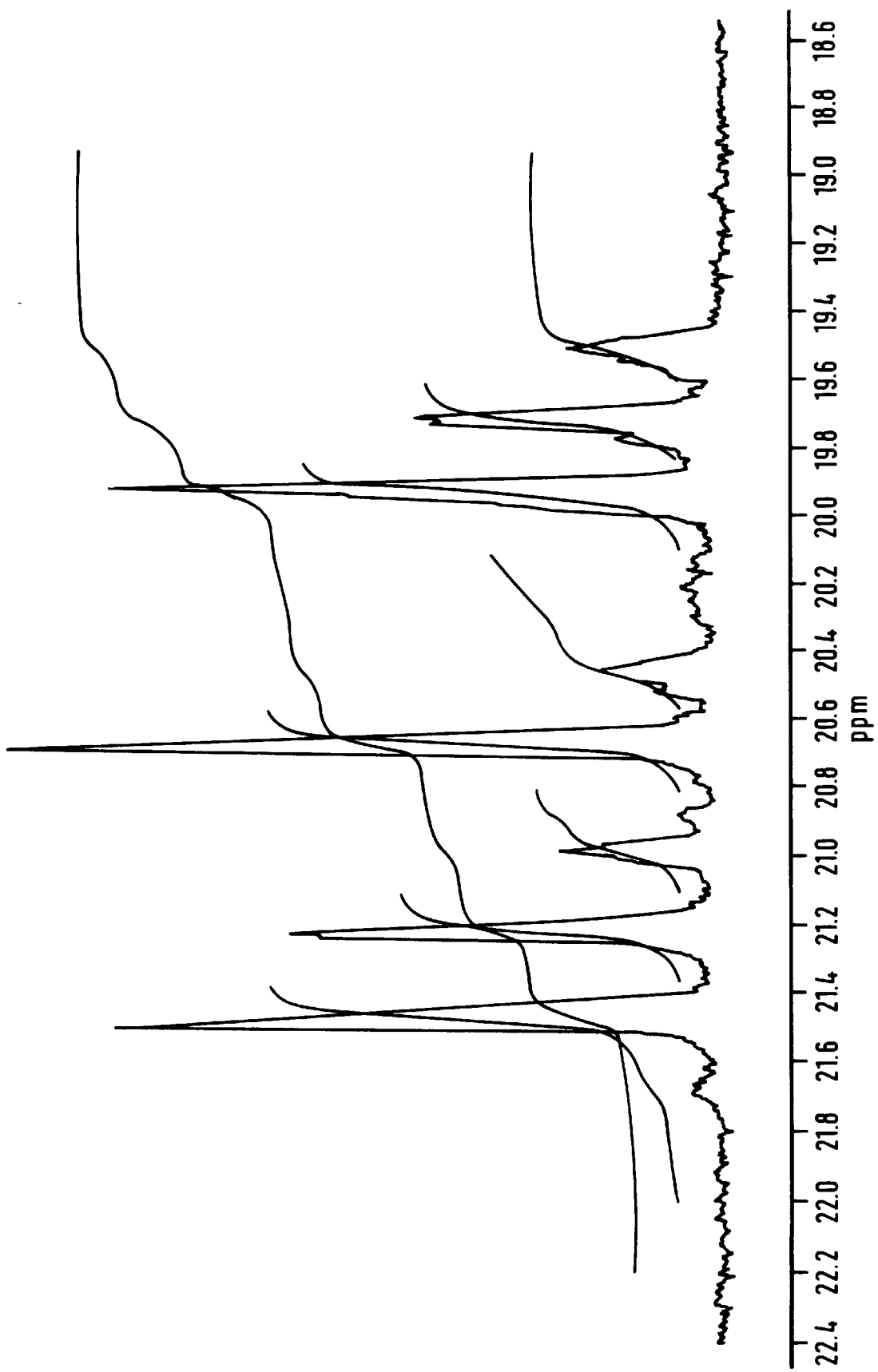

SYNDIO-ISOBLOCK POLYMER AND PROCESS FOR ITS PREPARATION

This is a continuation of Ser. No. 07/927,869, filed Aug. 10, 1992, now abandoned, which is a divisional application of Ser. No. 07/525,096 filed May 17, 1990 now abandoned.

The invention relates to a syndio-isoblock polymer having long isotactic and syndiotactic sequences and to a process for its preparation.

It is known that polypropylene exists in various structural isomers:

(a) highly isotactic polypropylene in whose molecular chains almost all of the tertiary carbon atoms have the same configuration, (b) isotactic stereoblock PP in whose molecular chains isotactic blocks of opposite configuration alternte with each other in a regualr manner, (c) syndiotactic polypropylene in whose molecular chains every second tertiary cartona tom has the same configuration, (d) atactic polypropylene in whose molecular chains the tertiary carbon atoms have a random configuration (e) atactic-isotactic stereoblock PP in whose molecular chains isotactic and atactic blocks alternate iwht each other, and (f) isoblocks PP whose molecular chains contain isotactic blocks which are spearated form one anotehr by a tertiary carbona tom having, in each case, the opposite configuration relative to the isotactic blocks.

A process for the preparation of isotactic stereoblock polymers is known in which propylene is polymerized using a metallocene of a metal form group IVb, Vb or VIb of the Periodic Table (cf. U.S. Pat. No. 4,522,982. This metallocene is a mono-, di- or tricyclopentadienyl or substituted cyclopentadienyl metal compound, in particular of titanium.

The cocatalyst used is an aluminoxane.

However, in dilute solution the titanocenes which are preferably used are insufficiently heat-stable for use in an industrial process. Moreover, in this process, products having a relatively long urn of isotactic sequences (n greater than 6) are only obtained at very low temperatures (–60° C.). Finally, the cocatalysts must be used in relatively high concentrations to achieve an adequate catalyst yield, with the consequence that the catalysts residues contained int he polymer product must be removed in a separate purification step.

Furthermore, it is known that stereoblock polymers of 1-olefins having long isotactic sequences can be obtained at industrially appropriate polymerization temperatures by means of a catalyst which is composed of a metallocene compound containing cyclopentadienyl radicals which are substituted by chiral groups, and an aluminoxane (cf. EP 269,987).

Moreover, it is known that stereoblock polymers of 1-olefins having a broad uni- or multi-modal molecular weight distribution can be obtained if the polymerization of the 1-olefins is carried out using a catalyst which is composed of a bridged chiral metallocene and an alumin-oxane (cf. EP 269,986). These polymers are particularly suitable for the preparation of transparent films.

It is also known that the use of a catalyst based on bis-cyclopentadienyl compounds of zirconium and an aluminoxane in the polymerization of propylene gives only atactic polymer (cf. EP 69,951).

Moreover, using soluble stereoridgid chiral zirconium compounds, it is possible to prepare highly isotactic polypropylene (cf. EP 185,918).

Finally, isoblock polymers have been proposed.

A plymerization process has been found in which a polymer having a regular molecular structure and a high molecular weight is obtaned at industrially appropriate process temperatures in a high yield.

The present invention accordingly provides a syndio-isoblock polymer of a 1-olefin of the formula RCH=CHR' in which R and R' are identical or different and are an alkyl radical having 1 to 14 carbona toms or R and R', with the carbon atoms joining them. form a rign, and the siad polymer has molecular chains in which syndiotactic and isotactic sequences are present and the sequence length is 3 to 50 monomer units.

Furthermore, the invention provides a process for the preparation of the abovementioned syndio-isoblock polyers by polymerization of a 1-olefin of the formula RCH=CHR' in which R and R' have the abovementioned meaning, at a temeprature of –60 to 100°C., a pressure of 0.5 to 100 bar, in solution, suspension or in the gas phase, in the presence of a catalyst which is composed of a metallocene and an aluminoxane, wherein the metallocene is a compound of the formula I

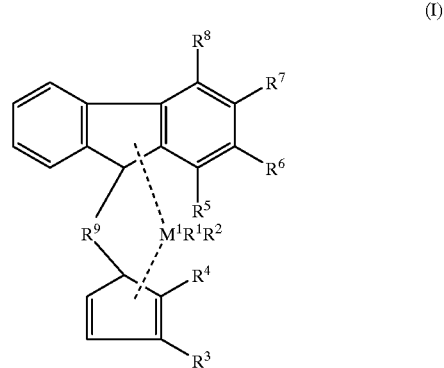

(I)

in which $M^1$ is titanium, zicrconioum, hafnium, vandadium, niobium or tantalum, $R^1$ and $R^2$ are identical or differenct and are a hydrogen atom, a halogen atom, $C_1$–$C_{10}$-alkyl, $C_1$–$C_{10}$-alkoxy, $C_6$–$C_{10}$-aryl, $C_6$–$C_{10}$-aryloxy, $C_2$–$C_{10}$-alkenyl, $C_7$–$C_{40}$-arylalkyl, $C_7$–$C_{40}$-alkylaryl or $C_8$–$C_{40}$-arylalkenyl, $R^3, R^4, R^5, R^6, R^7$ and $R^8$ are identical or different and are a hydrogen atom, $C_1$–$C_{10}$alkenyl, $C_7$–$C_{40}$-arylalkyl, $C_7$–$C_{40}$-alkylaryl or $C_8$–$C_{40}$-arylalkenyl, $R^3R^4, R^5R^6, R^7$ and $R^8$ are identical or different and are a hydrogen atom, $C_1$–$C_{10}$-alkyl, $C_1$–$C_{10}$-alkoxy, $C_6$–$C_{10}$-aryl, $C_6$–$C_{10}$; -aryloxy, $C_2$–$C_{10}$-alkenyl, $C_7$–$C_{40}$-arylalkyl, $C_7$–$C_{40}$-alkylaryl, $C_8$–$C_{40}$-arylalkenyl or a halogen atom, $R^9$ is

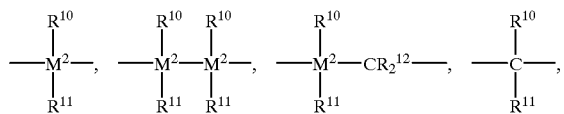

-continued

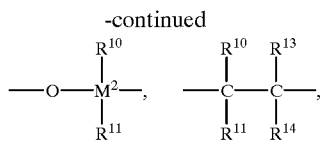

$=BR^{10}$, $=AlR^{10}$, —Ge—, —Sn—, —O—, —S—, =SO, $=SO_2$, $=NR^{10}$, =CO, $=PR^{10}$ or $=P(O)R^{10}$, where $R^{10}$, $R^{11}$, $R^{12}$, $R^{13}$ and $R^{14}$ are identical or different and are a hydrogen atom, a halogen atom, a $C_1$–$C_{10}$-alkyl, $C_1$–$C_{10}$-fluoroalkyl, $C_6$–$C_{10}$-fluoroaryl, $C_6$–$C_{10}$-aryl, $C_1$–$C_{10}$-alkoxy, $C_2$–$C_{10}$-alkenyl, $C_7$–$C_{40}$-arylalkyl, $C_8$–$C_{40}$-aryl-alkenyl, or $C_7$–$C_{40}$ -alkylaryl, or $R^{10}$ and $R^{11}$, or $R^{10}$ and $R^{12}$, together in each case with the atoms joining them, form a ring, and $M^2$ is silicon, germanium or tin.

The catalyst to be used in the process according to the invention is composed of an aluminoxane, and a metallocene of the formula I

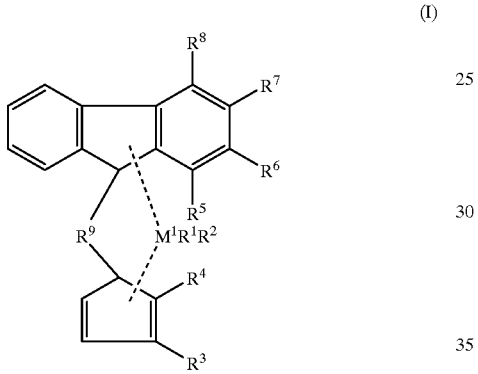

(I)

In formula I, $M^1$ is a metal from the group which includes titanium, zirconium, hafnium, vanadium, niobium and tentalum, preferably zirconium or hafnium.

$R^1$ and $R^2$ are identical or different and are a hydrogen atom, $C_1$–$C_{10}$-, preferably $C_1$–$C_3$-alkyl, $C_1$–$C_{10}$-, preferably $C_1$–$C_3$-alkoxy, $C_6$–$C_{10}$-, preferably $C_6$–$C_8$-aryl, $C_6$–$C_{10}$-, preferably $C_6$–$C_8$-aryloxy, $C_2$–$C_{10}$-, preferably $C_2$–$C_4$-alkenyl, $C_7$–$C_{40}$-, preferably $C_7$–$C_{10}$-arylalkyl, $C_7$–$C_{40}$-, preferably $C_7$–$C_{12}$ -alkylaryl, $C_8$–$C_{40}$-, preferably $C_8$–$C_{12}$-arylalkeny or a halogen atom, preferably chlorine.

$R^4$ $R^5$, $R^6$, $R^7$ adn $R^8$ are identical or different and are a hydrogen atom, $C_1$–$C_{10}$-, preferably $C_1$–$C_3$-alkyl, particularly preferably methyl (in the case of $R^3$) and H (in the cases of $R^4$, $R^5$, $R^6$, $R^7$ and $R^8$).

$R^9$ is a one- or multi-membered bridge and is

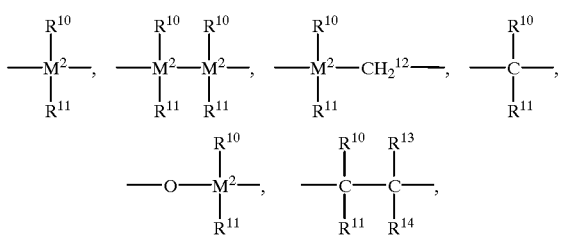

$=BR^{10}$, $=AiR^{10}$, —Ge—, —Sn—, —O—, —S—, =SO, $=SO_2$, $=NR^{10}$, =CO, $=PR^{10}$ or $=P(O)R^{10}$, while $R^{10}$, $R^{11}$, $R^{12}$, $R^{13}$ and $R^{14}$ are identical or different and ar e a hydrogen atom, a halogen atom, preferably chlorine, $C_1$–$C_{10}$-, preferably $C_1$–$C_3$-alkyl, in particular methyl or ethyl, $C_1$–$C_{10}$-fluoroalkyl, preferably a $CF_3$ group, $C_6$–$C_{10}$-fluoroaryl, preferably pentafluorophenyl, $C_6$–$C_{10}$-, preferably $C_6$–$C_8$-aryl, $C_1$–$C_{10}$-, preferably $C_1$–$C_4$-alkoxy, in particular methoxy, $C_2$–$C_{10}$-, preferably $C_2$–$C_4$-alkenyl, $C_7$–$C_{40}$-, preferably $C_7$–$C_{10}$-aryl-alkyl, $C_8$–$C_{40}$-, preferably $C_8$–$C_{12}$-arylalkenyl or $C_7$–$C_{40}$-, preferably $C_7$–$C_{12}$-alkylaryl, or $R^{10}$ and $R^{11}$, or $R^{10}$ and $R^{12}$, together in each case with the atoms joining them, form a ring.

$M^2$ is silicon, germanium or tin, preferably silicon or germanium.

$R^9$ is preferably $=CR^{10}R^{11}$, $=SiR^{10}R^{11}$, $=Ger^{10}R^{11}$, —O—, —S—, =SO, $=PR^{10}$ or $=P(O)R^{10}$.

the metallocense described above can be prepared by the following general reaction scheme:

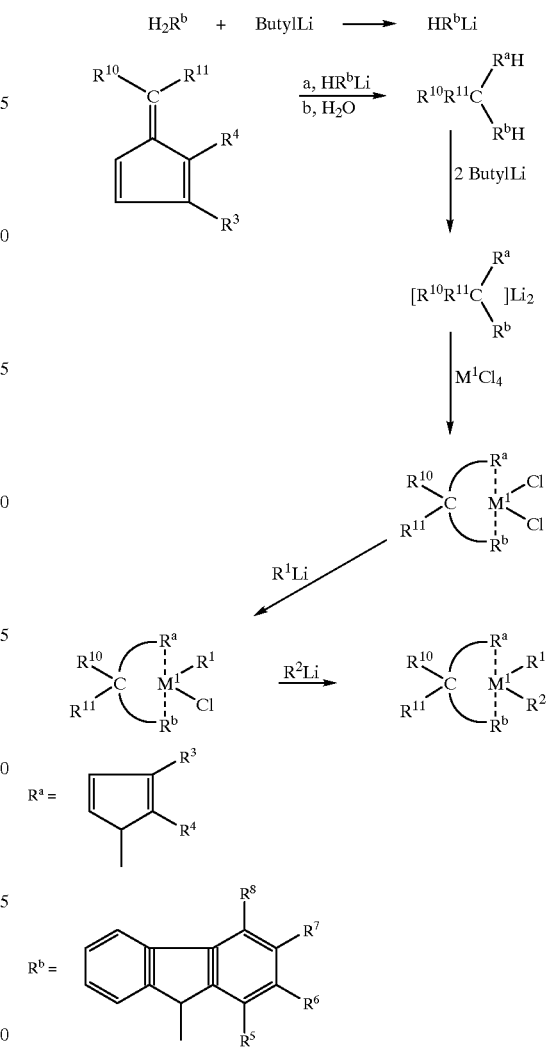

Preference is given to the use of metallocense such as dimethylmethylene-(9-fluorenyl)-3-methyl-(cyclopentadienyl)zircomium dichloride and (dimethylmethylene)-(9-fluorenyl)-3-methyl-(cyclopentadienyl)hafnium dichloride.

The cocatalyst is an aluminoxane of the formula II

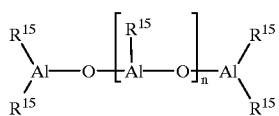

(II)

in the case of the linear type and/or of the formula III

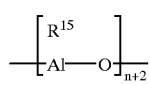

(III)

in the case of the cyclic type. In these formulae, $R^{15}$ is $C_1$–$C_6$-alkyl, preferably methyl, ethyl or isobutyl, butyl or neopentyl, or phenyl or benzyl. Particular preference is given to methyl. n is an integer from 2 to 50, preferably 5 to 40. However, the exact structure of the aluminoxane is unknown.

The aluminoxane can be prepared by various methods.

One possibility is the careful addition of water to a dilute solution of a trialkylaluminum by adding the solution of trialkylaluminum, preferably trimethylaluminum, and the water each in small protions to a previously introduced, comparatively large amount of an inert solvent and waiting between additions ofr gas evolution to cease.

According to another method, finely pulverized copper sulfate pentahydrate is formed into a slurry in toluene and to this slurry, in a glass flask under inert gas at about $-20°C.$, sufficient trialkylaluminum is added to give about 1 mol of $CuSO_4.5H_2O$ for every 4 gram-atoms of Al. After slow hydrolysis with elimination of alkane, the reaction mixture is allowed to remain at room temperature for 24 to 48 hours with colling if necessary so that the temeprature does not rise above $30°$ C. Then the aluminoxane dissolved in toluene is filtered off from the copper sulfate and the solution is concentrated in vacuo. In this method of preparation, it is assumed that the low molecular weight aluminoxanes condense to form higher oligomers with the liminaito of trialkyl aluminum.

Furthermore, aluminoxanes are obtained if a trialkyl-aluminum, preferably trimethylaluminum, dissolved in an inert aliphatic or aromatic solvent, preferably heptane or toluene, is reacted at a temperature of $-20$ ot $100°$ C. with aluminum salts containing water of crystallization, preferably aluminum sulfate. In this reaction, the volume ratio of solvent to the alklaluminum used is 1:1 to 50:1, preferably 5:1, and the reatio time, which can be monitored form elimination of the alkane, is 1 to 200 hours, preferably 10 to 40 hours.

Particular preference is given to hydrated aluminum salts whose content of water of crystallization is high. Special preference is given tohydrated aluminum sulfate, in particular the compoiunds $Al_2(SO_4)_3.16H_2O$ and $Al_2(SO_4)_3.18H_2O$ which have a prticularly high content of water of crystallization of 16 and 18 mol $H_2O$/mol $Al_2(SO_4)_3$.

A further variant of the preparatio of aluminoxanes is to dissolve trialkylaluminum, preferably trimethyl-aluminum, in the suspending medium, preferably inliquid monomers, in heptane or toluene, which ahs been previously charged into the polymerizatio vesseland then to react the aluminum compound with water.

There are other usable methods besides those whic have been described above for the preparation of aluminoxanes.

Whatever the manner of preparation, all aluminoxane solutions have in common a varying amount of unconverted trialkylaluminum which is present in the free form or as an adduct. This component has a still incompletely explained influence on the catalytic efficiency, which influence varies according to the metallocene compound used.

It is possible to preactivate the metallocene before use in the polymerization reaction using an aluminoxane of the formula II and/or III. This significantly increases the polymerizatio activity and improves the particle morphology.

the preactivatio of the transisito metal compound os carried out in solution. In this preactivation, the metallocene is preferably dissolved in a solution of the aluminoxane in an inert hydrocarbon. Suitable inert hydrocarbons ar ealiphatic or aromatic hydrocarbons. Preference is given to the use of toluene.

The concentration of the aluminoxane in the solution is in the range from about 1% by wieght up to the saturation limit, preferably from 5 to 30% by wieght, relative in each case to the overall solution. The metallocene can be used int he same concentration, but preferably it is used in an amount form $10^{-4}$–1 mol per mol of aluminoxane. the preactivation time is 5 minutes ot 60 hours, preferably 5 to 60 minutes. The operation is carried out at a temperature from $-78°$ C. to $100°$ C., preferably 0 to $70°$ C.

It is possible ot preactivate over a significantly longer period but normally this neither increases nor decreases the activity although it can be very convenient for storage purposes.

The polymerization is carried out in a known manner in solution, in suspension or in the gas phase, continuously or batchwide, in one or more steps at a temperature of $-60$ to $200°C.$, preferably $-30$ to $100°$ C., in particular 0 to $80°$ C.

The overall pressure in the polymerization systme is 0.5 to 100 bar. Preference is given to polymerization in the industrially particularly interesting pressure range of from 5 to 60 bar. Monomers whose boiling point is higer than the polymerizatio temerpature are preferably poolymerized at atmospheric pressure.

In this process, the metallocene compound is used at a concentration, relative to the transistion metal, of $10^{-3}$ to $10^{-7}$, preferably $10^{-4}$ to $10^{-6}$ mol of transition metal per $dm^3$ of solvent or per $dm^3$ of reactor volume. The aluminoxane is used at a concentration of $10^{-5}$ to $10^{-1}$ mol, preferably $10^{-5}$ to $10^{-2}$ mol per $dm^3$ of solvent or per $dm^3$ of reactor volume. In princople, however, it is also possible to use higher concentrations.

If the polymerization is carried out in suspension or in solution, an inert solvent of the type used for the Ziegler low pressure process is employed. The operation is carried out, for example, in an aliphatic or cycloaliphatic hydrocarbon; examples of these are butane, pentane, hexane, heptane, isoctane, cyclohexane and methylcyclohexane.

Furthermore, a goasoline fraction or hydrogenated diesel oil fraction can be used. It is also possible to use toluene. Preference is given to polymerization in the liquid monomer.

The monomers polymerized or copolymerized ar eolefins of the formula RC=CHR' is which R and R' ar eidentical or different and are a hydrogen atom or an alkyl radical having 1 to 14 carbon atoms or R and R' combine with the carbon atoms joining them together to form a ring. Examples of olefins of this type are ethylene, propylene, 1-butene, 1-hexene, 4-methyl-1-pentene, 1-octene, norbornene, norbornadine or compounds of the type 1,4,5,8-dimethano-1,2,3,4,4a,5,8,8a-octahydronaphthalene, 2-ethyl-1,4,5,8-dimethan-1,2,3,4,4a,5,8,8a-octahydronaphthalene or 2,3-dimethyl-1,4,5,8-dimethano-1,2,3,4,4a, 5,8,8a- octahydronaphthalene. Preference is given to propylene, 1-butene and norbonrnene.

The polymerization can be carried on for any desired period, since the catalyst system which is to b eused according to the invention ahs only a slight time-dependent decline in polymerization activity.

A feature of the process according to the invention is that the preferably used zirconium and hafnium compounds are very heat stable so that they can be employed even at temperatures of up to 90° C. Moreover, th ealuminoxanes used as cocatalysts can be added at lower concentrations than hitherto. Finally it is now possible to prepare syndio-isoblock polymers at industrially interesting temperatures.

The syndio-isoblock polymer according to the invention is a polymer of a 1-olefin of the formula R—CH═CHR' in which R and R' have the meaning given above, The polymer is, in particular, a propylene polymer.

The molecular chains of this polymer contian isotactic and syndiotactic sequences, Preferably, the molecular chains contain only isotactic and syndiotactic sequences.

BRIEF DESCRIPTION OF THE DRAWINGS

The polymer is characterized precisely using a $^{13}C$—NMR spectrum as shown in the Figure.

Owing to this steric structure, th esyndio-isoblock polymers accoridng to the invention are amosphous or partly crystalline depending on the molecular weight and on the syndiotactic and isotactic sequence length. Depending on the cyrstallinity, the polymes are obtained in the form of particulate powders, compact materials or liquids. The partly crystalline syndio-isoblock polymers have a lower melting point in comparison with isotactic polymers. Syndio-isoblock polymers have some rubber-like properties.

The invention is explained using the following examples. Symobols used have the following meanings:
VN=viscosity number in $cm^3/g$
M=weight-average molecular weight in g/mol
$M_w/M_n$=polydispersity determined using gel permeation chromatography (GPC) and
II=isotacticity index, determined using $^-C$—NMR spectroscopy
$n_{iso}$=average length of isotactic sequences
$n_{syn}$=average length of syndiotactic sequences.

EXAMPLE 1

Isopropylidene-(9-fluorenyl-3-methylcyclopentadienyl)-hafnium dichloride 6.9 g (41.6 mmol) of fluorene were dissolved in 30 $cm^3$ of THF and to this solution were added 41.6 mmol of a 2.5 molar solution of butyllithium in hexane. After stirring for 15 min, the solution was added at 0° C. to a solution of 5.0 g (41.6 mmol) of 2,6,6-trimethylfulvene in 30 $cm^3$ of THF and the mixture was stirred overnight. 40 $cm^3$ of water were added adn then the batch was extracted with ether. The organic phase was dried over $MgSO_4$ and concentrated. A total of 5.8 g (49%) of isopropyl-(-9-fluorenyl-3-methylcyclopentadiene) was crystallized at −35° C. in several fractions. The correct elemental analysis was obtained. The $^1H$-NMR spectrum revealed two isomers (3:1). The mass spectrum gave $M^+$=286. 3.79 g (13.3 mmol) of the ligand in 40 $cm^3$ of THF were added at 0° C. to 17.0 $cm^3$ (26.5 mmol) of a 1.6 molar butyl-lithium solution in hexane. After stirring for 30 min at room temperature, the solvent was evaporated off and the red residue washed repeatedly with hexane and dried under and oil pump vaccum for a lengthy period. 4.25 g (13.3 mmol) of $HfCl_4$ were suspended in 60 $cm^3$ of $CH_2Cl_3$ and to this suspension at −78° C. was added the dilithium salt. After being slowly warmed to room temeprature, the orange mixture was stirred for a further 2 h and then filtered through a G4 sinter. The filtrate was concentrated and left to crystallize at −35° C. 3.2 g (45%) of the hafnium complex were obtianed int heform of a yellowish orange powder. $^1H$—NMR spectrum (100 MHz, $CCCl_3$): 7.1–8.2 (m, 8, arom.H), 5.91, 5.55, 5.37 (3xdd, 3×1, CP—H), 2.38, 2.35 (2×5, 2×3, $C(CH_3)_2$), 2.11 (s, 3, Cp—$CH_3$). Correct elemental analyses. The mass spectrum gave $M^-$=534.

EXAMPLE 2

Isopropylidene-(9-fluorenyl-3-methylcyclopentadienyl)-zirconium dichloride

The syntheses of this compoins was carried out similarly to Example 1, 13.3 mmol of $ZrCl_4$ being used instead of the $HfCl_4$.

EXAMPLE 3

A dry 16 $dm^3$ vessel was purged with nitrogen and charged with 10 $dm^3$ of liquid propylene. then 30 $cm^3$ of a solution of methylaluminoxane in toluene (=MAO, equivalent to 46.7 mmol of Al, average degree of oligomerization n=30) were added and the batch was stirred for 15 minutes at 30° C.

In parallel with this, 96 mg (0.18 mmol) of fluorenyl-isopropylidene-2-methylcyclopentadienylhafnium dichloride were dissolved in 15 $cm^3$ of MAO solution (=23.3 mmol of Al) and preactivated by being left to stand for 15 minutes.

The solution was then added to the vessel. The polymerization system was brought to a temperature of 70° C. and then kept a this temperature for 3 hours.

This gave 0.47 kg of syndio-isoblock polymer. The activity of the metallocene was therefore 1.63 kg of polymer/g of metallocene/h.

the following analytical date were obtained form the polymer:
VN=140 $cm^3/g$, $M_w$=160, $900M_n$=67,000, $M_w/M_n$=2.4 $n_{syn}$=3.6, $n_{iso}$=3.5. p $^{13}C$—NMR spectropscopy revealed the following stereochemical pentad compositions in the polymer:
mmmm~18%, mmmr:~14%, rmmr:~5%, mmrr:~205, mmrm+rmrr: ~5%, mrmr:~05, rrrr:~19%, mrrr: ~13%, mrrm: ~75.

EXAMPLE 4

A method similar to Example 3 was followed. However, the polymerization temeprature selected was 60° C. The polymerization period was 5 hours. 70 mg of metallocene compound were used.

This gave 0.39 kg of syndio-isoblock polymer. Consequently, the activity of the metallocene was 0.93 kg of polymer/kg of metallocene was 0.93 kg of polymer/kg of metallocene/h.

The following analytical data were obtained form the polymer:
VN=266 $cm^3/g$, $M_w$=290,000, $M_n$=93,000, $M_w/M_n$=3.0 $n_{syn}$=3.8, $n_{iso}$=3.8,
mmmm: ~205, mmmr: ~135, rmmr: ~6%, mmrr: ~29%, mmrm+rmrr: ~5%, mrmr: ~05, rrr: ~21%, mrr: ~11%, mrrm: ~6%.

EXAMPLE 5

The method followed was similar to Example 1. However, the polymerization temperature selected was 50° C. The polymerizatio period was 4 hours. 51 mg of metallocene compound were used in the equivalent amount of MAO.

This gave 0.17 kg of syndio-isoblock polymer. The activity of the metallocene was therefore 0.83 kg of polymer/g of metallocene/h.

The following analytical data were obtained form the polymer:
VN=263 cm$^3$/g, $M_w$=330,000, $M_n$=110,000, $M_w/M_n$=3.0 $n_{syn}$=3.3, $n_{iso}$=3.7,
mmmm: ~21%, mmmr: ~145, rmmr: ~7%, mmrr: ~23%, mmrm+rmrr: ~2%, mrmr: –, rrrr: ~17%, mrrr: ~11%, mrrm: ~6%.

EXAMPLE 6

The method followed was similar to Example 1. However, the polymerizatio temerpature selected was 40° C. The polymerization period was 6 hours. 50 mg of metallocene compound were used.

This gave 0.11 kg of syndio-isoblock polymer. The acitvity of the metallocene was therefore 0.36 kg of polymer/kg of metallocene/h.

The following analytical data were obtained from the polymer:
VN=181 cm$^3$/g, $M_w$=240,000, $M_n$=58,000, $M_w/M_n$=4.1 $n_{syn}$=4.0, $n_{iso}$=3.9,
mmmm: ~18%, mmmr: ~13%, rmmr: ~6%, mmrr: ~23%, mmrm+rmrr: ~3%, mrmr: –, rrrr: ~19%, mrrr: ~12%, mrrm: ~6%.

EXAMPLE 7

The method followed was similar to Example 3. However, the polymerization temperature selected was 10° C. The polymerization period was 14 hours. 52 mg of metallocene compounds were used.

This gave 0.04 kg of syndio-isoblock polymer. The activity of the mettalocene was therefore 0.05 kg of polymer/g of metallocene/h.
VN=90 cm$^3$/g, $M_w$=97,000, $M_n$=32,000, $M_w/M_n$=3.0, $n_{syn}$=4.3, $n_{iso}$=3.6,
mmmm: ~17%, mmmr: ~13%, rmmr: ~5%, mmrr: ~24%, mmrm+rmrr: ~0.8%, mrmr: –, rrrr: ~21%, mrrr: ~13%, mrrm: ~6%.

EXAMPLE 8

A dry 16 dm$^3$ vessel was purged with nitrogen and charged with 10 dm$^3$ of liquid propylene. Then 30 cm$^3$ of a solution of methylaluminoxane in toluene (=MAO, equivalent to 46.7 mmol of Al, average degree of oligomerization n=30) were added and the batch was stirred for 15 minutes at 30° C.

In parallel with this, 20 mg (0.04 mmol) of fluorenylisopropylidene-2-methylcrclopentadienylzirconium dichloride were dissolved in 15 cm$^3$ of MAO (=23.3 mmol of Al) and preactivated by being left to stand for 15 minutes.

The solution was then added to the vessel. The polymerization system was brought to a temperature of 70° C. and then kept at this temperature for 3 hours.

This gave 0.91 kg of syndio-isoblock polymer. The activity of the metallocene was therefore 15.2 kg of polymer/g of metallocene/h.

The following analytical data were obtained from the polymer:
VN=12 cm$^3$/g, $M_w$=5,000, $M_n$=2,500, $M_w/M_n$=2.0, $n_{syn}$=3.7, $n_{iso}$=3.7.
$^{13}$C-NMR spectroscopy revealed the following stereochemical pentad compositions in the polymer:
mmmm: ~17%, mmmr: ~15%, rmmr: ~4%, mmrr: ~21%, mmrm+rmrr: ~6%, mrmr: –, rrrr: ~17%, mrrr: ~14%, mrrm: ~6%.

EXAMPLE 9

The method followed was similar to Example 8. However, the polymerization temperature selected was 60° C. The polymerization period was 5 hours. 35 mg of metallocene compound were used.

This gave 1.24 kg of snydio-isoblock polymer. The activity of the metallocene was therefore 7.03 kg of polymer/g of metallocene/h.

The following analytical data were obtained from the polymer:
VN=54 cm$^3$/g, $M_w$=47,250, $M_n$=22,500, $M_w/M_n$=2.1, $n_{syn}$=4.0, $n_{iso}$=4.1.
mmmm: ~21%, mmmr: ~14%, rmmr: ~4%, mmrr: ~20%, mmrm+rmrr: ~5%, mrmr: –, rrrr: ~20%, mrrr: ~10%, mrrm: ~8%.

EXAMPLE 10

The method followed was similar to Example 8. However, the polymerization temperature selected was 50° C. The polymerization period was 6 hours. 27 mg of metallocene compound were used.

This gave 0.9 kg of syndio-isoblock polymer. The activity of the metallocene was therefore 5.6 kg of polymer/g of metallocene/h.

The following analytical data were obtained from the polymer:
VN=54 cm$^3$/g, $M_w$=47,500, $M_n$=21,500, $M_w/M_n$=2.2, $n_{syn}$=3.7, $n_{iso}$=4.0,
mmmm: ~20%, mmmr: ~13%, rmmr: ~6%, mmrr: ~24%, mmrm+rmrr: ~2%, mrmr: –, rrrr: ~18%, mrrr: ~13%, mrrm: ~4%.

EXAMPLE 11

The method followed was similar to Example 8. However, the polymerization temperature selected was 40° C. The polymerization period was 4 hours. 25 mg of metallocene compound were used.

This gave 0.45 kg of syndio-isoblock polymer. The activity of the metallocene was therefore 4.5 kg of polymer/g of metallocene/h.

The following analytical data were obtained from the polymer:
VN=60 cm$^3$/g, $M_w$=54,600, $M_n$=21,700, $M_w/M_n$=1.9, $n_{syn}$=3.7, $n_{iso}$=3.7.
mmmm: ~16%, mmmr: ~12%, rmmr: ~8%, mmrr: ~25%, mmrm+rmrr: ~2%, mrmr: –, rrrr: ~20%, mrrr: ~11%, mrrm: ~6%.

EXAMPLE 12

The method followed was similar to Example 8. However, the polymerization temperature selected was 10° C. The polymerization period was 16 hours. 50 mg of metallocene compound were used.

This gave 0.4 kg of syndio-isoblock polymer. The activity of the metallocene was therefore 0.5 kg of polymer/g of metallocene/h.

The following analytical data were obtained from the polymer:

VN=52 cm$^3$/g, M$_w$=44,000, M$_n$=17,000, M$_w$/M$_n$=2.6, n$_{syn}$=4.5, n$_{iso}$=4.4.

mmmm: ~19%, mmmr: ~14%, rmmr: ~5%, mmrr: ~22%, mmrm+rmrr: ~0.8%, mrmr: –, rrrr: ~20%, mrrr: ~13.2%, mrrm: ~6%.

What is claimed is:

1. A process for the preparation of a syndio-isoblock polymer having molecular chains in which syndiotactic and isotactic sequences are present and the sequence length is 3 to 50 monomer units by polymerization of propylene or an olefin of the formula RCH=CHR' in which R and R' are identical or different and are an alkyl radical having 1 to 14 carbon atoms or R and R' combine with the carbon atoms joining them together to form a ring at a temperature of –60 to 100° C., a pressure of 0.5 to 100 bar, in solution, in suspension or in the gas phase, in the presence of a catalyst which is composed of a metallocene and an aluminoxane, wherein the metallocene is a compound of the formula I

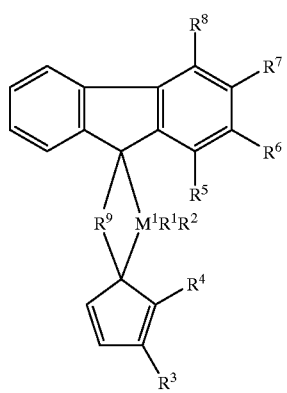

(I)

in which

M$^1$ is titanium zirconium, hafnium, vanadium, niobium or tantalum,

R$^1$ and R$^2$ are identical or different and are a hydrogen atom, a halogen atom, C$_1$–C$_{10}$-alkyl, C$_1$–C$_{10}$-alkoxy, C$_6$–C$_{10}$-aryl, C$_6$–C$_{10}$-aryloxy, C$_2$–C$_{10}$-alkenyl, C$_7$–C$_{40}$-arylalkyl, C$_7$–C$_{40}$-alkylaryl or C$_8$–C$_{40}$-arylalkenyl, R$^3$, R$^4$, R$^5$, R$^6$, R$^7$ and R$^8$ are identical or different and are a hydrogen atom, C$_1$–C$_{10}$-alkyl, C$_1$–C$_{10}$-alkoxy, C$_6$–C$_{10}$-aryl, C$_6$–C$_{10}$-aryloxy, C$_2$–C$_{10}$-alkenyl, C$_7$–C$_{40}$-arylalkyl, C$_7$–C$_{40}$-alkylaryl, C$_8$–C$_{40}$-arylalkenyl or a halogen atom, with the proviso that at least one of the substitutents R$^3$ through R$^8$ is not hydrogen, R$^9$ is

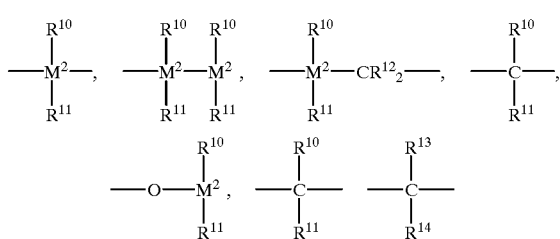

=BR$^{10}$, =AlR$^{10}$, —Ge—, —Sn—, —O—, —S—, =SO, =SO$_2$, =NR$^{10}$, =CO, =PR$^{10}$ or =P(O)R$^{10}$, where R$^{10}$, R$^{11}$, R$^{12}$, R$^{13}$ and R$^{14}$ are identical or different and are a hydrogen atom, a halogen atom, a C$_1$–C$_{10}$-alkyl, C$_1$–C$_{10}$-fluoroalkyl, C$_6$–C$_{10}$-fluoroaryl, C$_6$–C$_{10}$-aryl, C$_1$–C$_{10}$-alkoxy, C$_2$–C$_{10}$-alkenyl, C$_7$–C$_{40}$-arylalkyl, C$_8$–C$_{40}$-arylalkenyl, or C$_7$–C$_{40}$-alkylaryl, or R$^{10}$ and R$^{11}$, or R$^{10}$ and R$^{12}$, together in each case with the atoms joining them, form a ring, and M$^2$ is silicon, germanium or tin.

2. The process as claimed in claim 1, wherein propylene is polymerized.

3. The process as claimed in claim 1, wherein M$^1$ is zirconium or hafnium.

4. The process as claimed in claim 1, wherein R$^3$, R$^4$, R$^5$, R$^6$, R$^7$ and R$^8$ are identical or different and are hydrogen atom or C$_1$–C$_3$-alkyl.

5. The process as claimed in claim 1, wherein R$^9$ is selected from the group consisting of =CR$^{10}$R$^{11}$, =SiR$^{10}$R$^{11}$, =GeR$^{10}$R$^{11}$, —O—, —S—, =SO, =PR$^{10}$ and =P(O)R$^{10}$.

6. The process as claimed in claim 1, wherein the aluminoxane is of formula

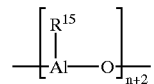

(III)

in the case of linear type and/or of the formula III

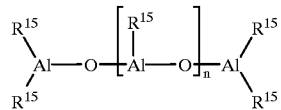

(II)

in the case of the cyclic type, wherein R$^{15}$ is a C$_1$–C$_6$-alkyl and n is an integer from 2 to 50.

7. The process as claimed in claim 6, wherein R$^{15}$ is selected from the group consisting of methyl, ethyl, isobutyl, butyl, neopentyl, phenyl and benzyl.

8. The process as claimed in claim 6, wherein n is an integer from 5 to 40.

9. A process for the preparation of a syndio-isoblock polymer having molecular chains in which syndiotactic and isotactic sequences are present and the sequence length is 3–50 monomer units by polymerization of propylene or an olefin of the formula RCH=CHR' in which R and R' are identical or different and are an alkyl radical having 1 to 14 carbon atoms or R and R' with the carbon atoms joining them, form a ring at a temperature of –60 to 100° C., a pressure of 0.5 to 100 bar, in solution, in suspension or in the gas phase, in the presence of a catalyst which is composed of a metallocene and an aluminoxane, wherein the metallocene is a compound of the formula I (I)

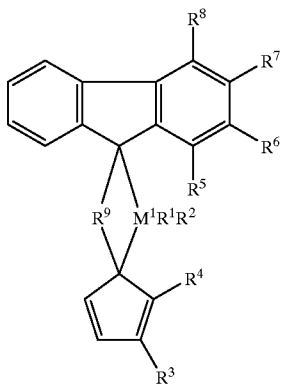

in which
M$^1$ is titanium, zirconium, hafnium, vanadium, niobium or tantalum,
R$^1$ and R$^2$ are identical or different and are hydrogen atom, a halogen atom, C$_1$–C$_{10}$ alkyl, C$_1$–C$_{10}$-alkoxy, C$_6$–C$_{10}$-aryl, C$_6$–C$_{10}$-aryloxy, C$_2$–C$_{10}$-alkenyl, C$_7$–C$_{40}$-arylalkyl, C$_7$–C$_{40}$-alkylaryl or C$_8$–C$_{40}$-arylalkenyl,
R$^3$ is C$_1$–C$_{10}$-alkyl, R$^4$, R$^5$, R$^6$, R$^7$ and R$^8$ are identical or different and are a hydrogen atom, C$_1$–C$_{10}$-alkyl, C$_1$–C$_{10}$-alkoxy, C$_6$–C$_{10}$-aryl, C$_6$–C$_{10}$-aryloxy, C$_2$–C$_{10}$-alkenyl, C$_7$–C$_{40}$-arylalkenyl, C$_7$–C$_{40}$-alkylaryl, C$_8$–C$_{40}$-arylalkenyl or a halogen atom,
R$^9$ is

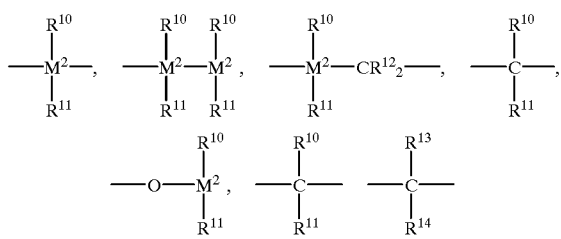

=BR$^{10}$, =AlR$^{10}$, —Ge—, —Sn—, —O—, —S—, =SO, =SO$_2$, =NR$^{10}$, =CO, =PR$^{10}$ or =P(O)R$^{10}$, where R$^{10}$, R$^{11}$, R$^{12}$, R$^{13}$ and R$^{14}$ are identical or different and are a hydrogen atom, a halogen atom, a C$_1$–C$_{10}$-alkyl, C$_1$–C$_{10}$-fluoroalkyl, C$_6$–C$_{10}$-fluoroaryl, C$_6$–C$_{10}$-aryl, C$_1$–C$_{10}$-alkoxy, C$_2$–C$_{10}$-alkenyl, C$_7$–C$_{40}$-arylalkyl, C$_8$–C$_{40}$-arylalkenyl, or C$_7$–C$_{40}$-alkylaryl, or R$^{10}$ and R$^{11}$, or R$^{10}$ and R$^{12}$, together in each case with the atoms joining them, form a ring and
M$^2$ is silicon, germanium or tin.

10. A process as claimed in claim 9, wherein R$^3$ is methyl.
11. A process as claimed in claim 9, wherein R$^4$, R$^5$, R$^6$, R$^7$ and R$^8$ are a hydrogen atom.
12. A process for the preparation of snydio-isoblock polymer having molecular chains in which syndiotactic and isotactic sequences are present and the sequence length is 3–50 monomer units by polymerization of propylene or an olefin of the formula RCH=CHR' in which R and R' are identical or different and are an alkyl radical having 1 to 14 carbon atoms or R and R' combine with the carbon atoms joining them together to form a ring at a temperature of –60 to 100° C., a pressure of 0.5 to 100 bar, in solution, in suspension or in the gas phase, in the presence of a catalyst which is composed of a metallocene and an aluminoxane, wherein the metallocene is a compound of the formula I (I)

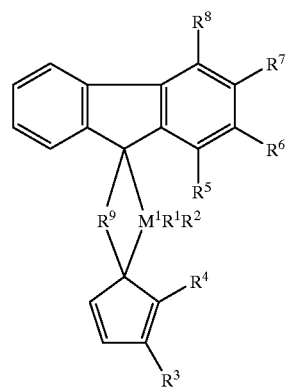

in which
M$^1$ is zirconim or hafnium,
R$^1$ and R$^2$ are chorine,
R$^3$ is methyl, R$^4$, R$^5$, R$^6$, R$^7$ and R$^8$ are a hydrogen atom, and
R$^9$ is

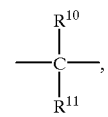

where R$^{10}$ and R$^{11}$ are C$_1$–C$_{10}$-alkyl.
13. The process as claimed in claim 1, wherein R$^3$ is C$_1$–C$_{10}$-alkyl or, in the case when R$^4$ is C$_1$–C$_{10}$-alkyl, then R$^3$ is hydrogen.
14. The process as claimed in claim 13, wherein R$^3$ is C$_1$–C$_{10}$-alkyl or, in the case when R$^4$ is methyl, then R$^3$ is hydrogen.
15. The process as claimed in claim 14, wherein R$^3$ is methyl and R$^4$ through R$^8$ are hydrogen.
16. The process as claimed in claim 1, wherein R$^1$ and R$^2$ are identical or different and are a halogen atom, R$^3$ is C$_1$–C$_{10}$-alkyl or, in the case when R$^4$ is methyl, then R$^3$ is hydrogen.
17. The process as claimed in claim 16, wherein R$^9$ is

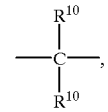

R$^{10}$ and R$^{11}$ are C$_1$–C$_{10}$-alkyl.
18. The process as claimed in claim 17, wherein R$^3$ is methyl and R$^4$-R$^8$ are hydrogen.
19. The process as claimed in claim 18, wherein M$^1$ is zirconium or hafnium.
20. A process for the preparation of a syndio-isoblock polymer having molecular chains in which syndiotactic and isotactic sequences are present and the sequence length is 3 to 50 monomer units by polymerization of an olefin of the formula RCH=CHR' in which R and R' are identical or different and are a hydrogen atom or an alkyl radical having 1 to 14 carbon atoms or R and R' combine with the carbon atoms joining them together to form a ring at a temperature of −60 to 100° C., a pressure of 0.5 to 100 bar, in solution, in suspension or in the gas phase, in the presence of a catalyst which is composed of a metallocene and an aluminoxane, wherein the metallocene is a compound of the formula I

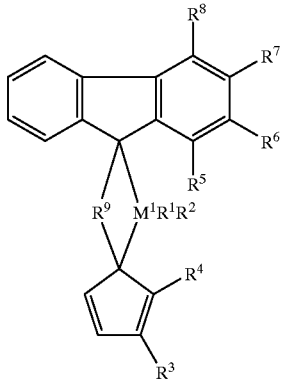

(I)

in which

M$^1$ is titanium zirconium, hafnium, vanadium, niobium or tantalum,

R$^1$ and R$^2$ are identical or different and are a hydrogen atom, a halogen atom, C$_1$–C$_{10}$-alkyl, C$_1$–C$_{10}$-alkoxy, C$_6$–C$_{10}$-aryl, C$_6$–C$_{10}$-aryloxy, C$_2$–C$_{10}$-alkenyl, C$_7$–C$_{40}$-arylalkyl, C$_7$–C$_{40}$-alkylaryl or C$_8$–C$_{40}$-arylalkenyl, R$^3$, R$^4$, R$^5$, R$^6$, R$^7$ and R$^8$ are identical or different and are a hydrogen atom, C$_1$–C$_{10}$-alkyl, C$_1$–C$_{10}$-alkoxy, C$_6$–C$_{10}$-aryl, C$_6$–C$_{10}$-aryloxy, C$_2$–C$_{10}$-alkenyl, C$_7$–C$_{40}$-arylalkyl, C$_7$–C$_{10}$-alkylaryl, C$_8$–C$_{40}$-arylalkenyl or a halogen atom, with the proviso that R$^3$ and R$^4$ are not hydrogen at the same time, R$^9$ is

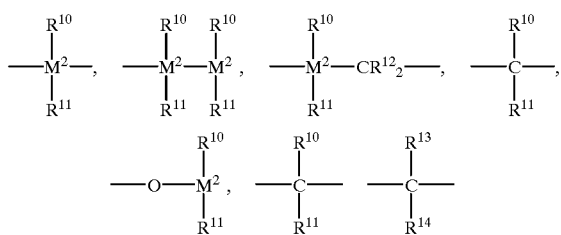

=BR$^{10}$, =AlR$^{10}$, —Ge—, —Sn—, —O—, —S—, =SO, =SO$_2$, =NR$^{10}$, =CO, =PR$^{10}$ or =P(O)R$^{10}$, where R$^{10}$, R$^{11}$, R$^{12}$, R$^{13}$ and R$^{14}$ are identical or different and are a hydrogen atom, a halogen atom, a C$_1$–C$_{10}$-alkyl, C$_1$–C$_{10}$-fluoroalkyl, C$_6$–C$_{10}$-fluoroaryl, C$_6$–C$_{10}$-aryl, C$_1$–C$_{10}$-alkoxy, C$_2$–C$_{10}$-alkenyl, C$_7$–C$_{40}$-arylalkyl, C$_8$–C$_{40}$-arylalkenyl, or C$_7$–C$_{40}$-alkylaryl, or R$^{10}$ and R$^{11}$, or R$^{10}$ and R$^{12}$, together in each case with the atoms joining them, form a ring, and M$^2$ is silicon, germanium or tin.

21. A metallocene used to make a catalyst to produce syndio-isoblock polymers having molecular chains in which syndiotactic and isotactic sequences are present and the sequence length is 3 to 50 monomer units by polymerization of an olefin of the formula RCH=CHR' in which R and R' are identical or different and are a hydrogen atom or an alkyl radical having 1 to 14 carbon atoms or R and R' combine with the carbon atoms joining them together to form a ring and said metallocene is a compound of the formula I

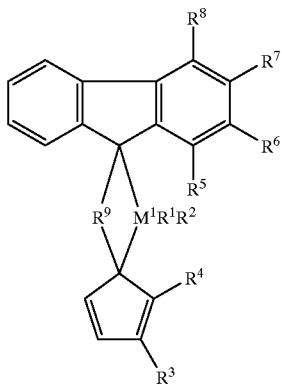

(I)

in which

M$^1$ is titanium zirconium, hafnium, vanadium, niobium or tantalum,

R$^1$ and R$^2$ are identical or different and are a hydrogen atom, a halogen atom, C$_1$–C$_{10}$-alkyl, C$_1$–C$_{10}$-alkoxy, C$_6$–C$_{10}$-aryl, C$_6$–C$_{10}$-aryloxy, C$_2$1 C$_{10}$-alkenyl, C$_7$–C$_{40}$-arylalkyl, C$_7$–C$_{40}$-alkylaryl or C$_8$–C$_{40}$-arylalkenyl, R$^3$, R$^4$, R$^5$, R$^6$, R$^7$ and R$^8$ are identical or different and are a hydrogen atom, C$_1$–C$_{10}$-alkyl, C$_1$–C$_{10}$-alkoxy, C$_6$–C$_{10}$-aryl, C$_6$–C$_{10}$-aryloxy, C$_2$–C$_{10}$-alkenyl, C$_7$–C$_{40}$-arylalkyl, C$_7$–C$_{40}$-alkylaryl, C$_8$–C$_{40}$-arylalkenyl or a halogen atom, with the proviso that R$^3$ and R$^4$ are not hydrogen at the same time, R$^9$ is

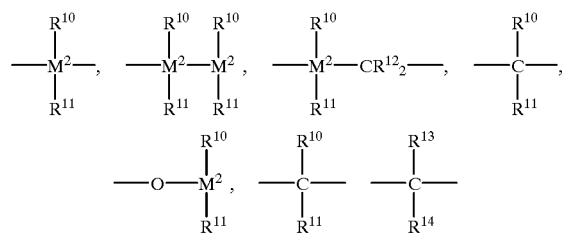

=BR$^{10}$, =AlR$^{10}$, —Ge—, —Sn—, —O—, —S—, =SO, =SO$_2$, =NR$^{10}$, =CO, =PR$^{10}$ or =P(O)R$^{10}$, where R$^{10}$, R$^{11}$, R$^{12}$, R$^{13}$ and R$^{14}$ are identical or different and are a hydrogen atom, a halogen atom, a C$_1$–C$_{10}$-alkyl, C$_1$–C$_{10}$-fluoroalkyl, C$_6$–C$_{10}$-fluoroaryl, C$_6$–C$_{10}$-aryl, C$_1$–C$_{10}$-alkoxy, C$_2$–C$_{10}$-alkenyl, C$_7$–C$_{40}$-arylalkyl, C$_8$–C$_{40}$-arylalkenyl, or C$_7$–C$_{40}$-alkylaryl, or R$^{10}$ and R$^{11}$, or R$^{10}$ and R$^{12}$, together in each case with the atoms joining them, form a ring, and M$^2$ is silicon, germanium or tin.

22. A metallocene catalyst comprising the metallocene as claimed in claim 21 and an aluminoxane and said metallocene catalyst produces a syndio-isoblock polymers having molecular chains in which syndiotactic and isotactic sequences are present and the sequence length is 3 to 50 monomer units.

23. The metallocene as claimed in claim 21, wherein said metallocene is isopropylidene-(9-fluorenyl-3- methylcyclopentadienyl)zirconium dichloride and said olefin is propylene.

24. The catalyst as claimed in claim 22, wherein said metallocene is isopropylidene-(9-fluorenyl-3-methylcyclopentadienyl)zirconium dichloride and said olefin is propylene.

25. The process as claimed in claim 20, wherein said olefin is ethylene or propylene.

26. The process as claimed in claim 20, wherein said olefin is a 1-olefin.

* * * * *

UNITED STATES PATENT AND TRADEMARK OFFICE
CERTIFICATE OF CORRECTION

PATENT NO. : 6,225,425 B1
DATED : May 1, 2001
INVENTOR(S) : Volker Dolle et al.

It is certified that error appears in the above-identified patent and that said Letters Patent is hereby corrected as shown below:

Column 12, claim 6,
Line 24, should appear as follows:
-- 6. The process as claimed in claim 1, wherein the aluminoxane is of the formula II

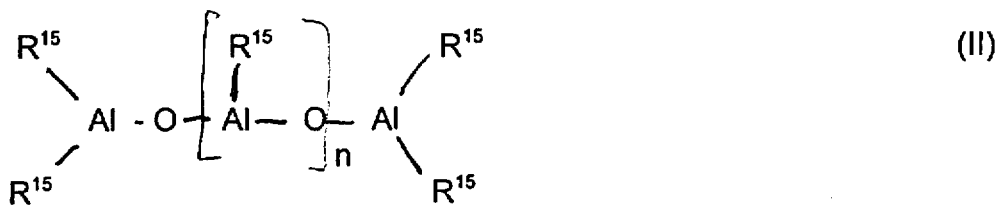

in the case of linear type and/or of the formula III

in the case of the cyclic type, wherein $R^{15}$ is a $C_1$-$C_6$-alkyl and n is an integer from 2 to 50. --

Column 14,
Line 23, "chorine" should read -- chlorine --.

Signed and Sealed this

Twenty-fifth Day of December, 2001

JAMES E. ROGAN
Director of the United States Patent and Trademark Office

Attest:

Attesting Officer